United States Patent
Korth et al.

(10) Patent No.: US 8,664,370 B2
(45) Date of Patent: Mar. 4, 2014

(54) PROCESS FOR PREPARING SILICON-CONTAINING AZODICARBAMIDES

(75) Inventors: Karsten Korth, Grenzach-Wyhlen (DE); Julia Keck, Hesshein (DE); Susann Witzsche, Rheinfelden (DE); Oliver Klockmann, Niederzier (DE); Jaroslaw Monkiewicz, Rheinfelden (DE); Christian Springer, Rheinfelden (DE)

(73) Assignee: Evonik Degussa GmbH, Essen (DE)

( * ) Notice: Subject to any disclaimer, the term of this patent is extended or adjusted under 35 U.S.C. 154(b) by 64 days.

(21) Appl. No.: 13/580,780

(22) PCT Filed: Mar. 11, 2011

(86) PCT No.: PCT/EP2011/053824
§ 371 (c)(1),
(2), (4) Date: Aug. 23, 2012

(87) PCT Pub. No.: WO2011/120792
PCT Pub. Date: Oct. 6, 2011

(65) Prior Publication Data
US 2013/0012691 A1    Jan. 10, 2013

(30) Foreign Application Priority Data
Mar. 29, 2010   (DE) .................. 10 2010 003 387

(51) Int. Cl.
*C09B 43/12*   (2006.01)
*C07F 7/18*   (2006.01)

(52) U.S. Cl.
USPC .......................................................... 534/591

(58) Field of Classification Search
None
See application file for complete search history.

(56) References Cited

U.S. PATENT DOCUMENTS

| 4,118,367 | A  | 10/1978 | Dawes |
| 7,777,063 | B2 | 8/2010  | Korth |
| 2009/0186961 | A1 | 7/2009 | Araujo da Silva |
| 2009/0221751 | A1 | 9/2009 | Hasse |
| 2009/0234066 | A1 | 9/2009 | Araujo da Silva |

FOREIGN PATENT DOCUMENTS

DE    2704506 A1    8/1977

OTHER PUBLICATIONS

International Report on Patentability and Written Opinion received in PCT/EP2011/053824, issued Oct. 2, 2012.
International Search Report received in PCT/EP2011/053824, mailed Jun. 28, 2011.
Written Opinion received in PCT/EP2011/053824, mailed Jun. 28, 2011.

*Primary Examiner* — Alicia L Otton
(74) *Attorney, Agent, or Firm* — Smith, Gambrell & Russell, LLP

(57) ABSTRACT

The invention relates to a process for preparing silicon-containing azodicarbamides of the general formula (I) $(R^1)_{3-a}(R^2)_a Si-R^I-NH-C(O)-N=N-C(O)-NH-R^I-Si(R^1)_{3-a}(R^2)_a$ (I), by reaction of azobiscarboxy compounds of the general formula II $R^3-X^1-C(O)-N=N-C(O)-X^1-R^4$ (II) with aminosilanes of the general formula III $(R^1)_{3-a}(R^2)_a Si-R^I-NH_2$ (III).

9 Claims, No Drawings

PROCESS FOR PREPARING SILICON-CONTAINING AZODICARBAMIDES

The invention relates to a process for producing silicon-containing azodicarbamides.

DE 2704506 discloses compounds of the general formula Y—X—CO—N=N—CO—X$^1$—Z and use thereof in filled rubber mixtures.

US 20090234066 A1 moreover discloses compounds of the A-CO—N=N—CO—Z-G type, which are used together with sulphur-containing silanes in rubber mixtures comprising isoprene rubber.

US 20090186961 A1 discloses compounds of the A-CO—N=N—CO—Z-G type, which are used together with coating materials in rubber mixtures comprising isoprene rubber.

It is an object of the present invention to provide a process which, in comparison with the processes of the prior art, needs fewer synthesis stages, does not require the oxidation of hydrazine derivatives, and can give high yields.

The invention provides a process for producing silicon-containing azodicarbamides of the general formula I $$(R^1)_{3-a}(R^2)_a Si—R^I—NH—C(O)—N=N—C(O)—NH—R^I—Si(R^1)_{3-a}(R^2)_a \quad (I),$$

via reaction of azobiscarboxy compounds of the general formula II $$R^3—X^1—C(O)—N=N—C(O)—X^1—R^4 \quad (II)$$

with aminosilanes of the general formula III $$(R^1)_{3-a}(R^2)_a Si—R^I—NH_2 \quad (III),$$

where a is mutually independently 1, 2 or 3, $R^1$ are mutually independently substituted or unsubstituted C1-C18-, preferably C1-C10-, particularly preferably C1-C6-, very particularly preferably C1-, alkyl groups, C5-C18-, preferably C6-, cycloalkyl groups, or C6-C18-aryl groups, preferably phenyl, $R^2$ are mutually independently an —OH, a substituted or unsubstituted C1-C18-alkoxy group, preferably $CH_3$—O—, $C_2H_5$—O—, $C_3H_7$—O—, $C_{12}H_{25}$—O—, $C_{14}H_{29}$—O—, $C_{16}H_{33}$—O—, $C_{18}H_{37}$—O—, or particularly preferably $C_2H_5$—O—, or a C5-C18-cycloalkoxy group, $R^I$ is a branched or unbranched, saturated or unsaturated, aliphatic, aromatic or mixed aliphatic/aromatic divalent $C_1$-$C_{30}$-, preferably $C_1$-$C_{20}$-, particularly preferably $C_1$-$C_{10}$-, very particularly preferably $C_1$-$C_7$-, hydrocarbon group, if appropriate substituted with F—, Cl—, Br—, I—, —CN or HS—, $X^1$ are mutually independently O, NH or N-$A^1$, where $A^1$ is a C1-C12-, preferably C1-C4-, particularly preferably C1-, alkyl group or aryl group, preferably phenyl or substituted phenyl, and $R^3$ and $R^4$ are mutually independently an H, a C1-C18-alkyl group, preferably methyl, ethyl or isopropyl, a benzyl group (—$CH_2$—$C_6H_5$) or an alkyl polyether group ($CH_2$—$CH_2$—O)$_n$—$R^5$ or (CH($CH_3$)—$CH_2$—O)$_n$—$R^5$, preferably methyl-(O—$CH_2$—$CH_2$)$_n$—, ethyl-(O—$CH_2$—$CH_2$)$_n$—, propyl-(O—$CH_2$—$CH_2$)$_n$—, butyl-(O—$CH_2$—$CH_2$)$_n$— or hexyl-(O—$CH_2$—$CH_2$)$_n$—, where the average of n is from 1 to 18, preferably from 1 to 10, particularly preferably from 1 to 8, very particularly preferably from 1 to 5, and $R^5$ is mutually independently a branched or unbranched, saturated or unsaturated monovalent C1-C32-, preferably C2-C25-, particularly preferably C3-C18-, hydrocarbon chain.

Silicon-containing azobiscarbamides can be mixtures of silicon-containing azobiscarbamides of the general formula I.

The product of the process can comprise oligomers produced via hydrolysis and condensation of the alkoxysilane functions of the silicon-containing azobiscarbamides of the general formula I.

The azobiscarboxy compound used as starting material can be a mixture of azobiscarboxy compounds of the general formula II.

The aminosilane used as starting material can be a mixture of aminosilanes of the general formula III.

The aminosilanes used can comprise oligomers produced via hydrolysis and condensation of the alkoxysilane functions of the aminosilanes of the general formula III.

$R^1$ can preferably be —$CH_2$—, —$CH_2CH_2$—, —$CH_2CH_2CH_2$—, —$CH_2CH_2CH_2CH_2$—, —CH($CH_3$)—, —$CH_2CH(CH_3)$—, —CH($CH_3$)$CH_2$—, —C($CH_3$)$_2$—, —CH($C_2H_5$)—, —$CH_2CH_2CH(CH_3)$—, —CH($CH_3$)$CH_2CH_2$—, —$CH_2CH(CH_3)CH_2$—, —$CH_2CH_2CH_2CH_2CH_2$—, —$CH_2CH_2CH_2CH_2CH_2CH_2$—, —$CH_2CH_2CH_2CH_2CH_2CH_2CH_2$—, —$CH_2CH_2CH_2CH_2CH_2CH_2CH_2CH_2$—, —$CH_2CH_2CH_2CH_2CH_2CH_2CH_2CH_2CH_2$—, —$CH_2CH_2CH_2CH_2CH_2CH_2CH_2CH_2CH_2CH_2$—, —$CH_2CH_2CH_2CH_2CH_2CH_2CH_2CH_2CH_2CH_2CH_2$—, —$CH_2CH_2CH_2CH_2CH_2CH_2CH_2CH_2CH_2CH_2CH_2CH_2$—, —$CH_2CH_2CH_2CH_2CH_2CH_2CH_2CH_2CH_2CH_2CH_2CH_2CH_2$—, —$CH_2CH_2CH_2CH_2CH_2CH_2CH_2CH_2CH_2CH_2CH_2CH_2CH_2CH_2$— or —$CH_2$—$\langle C_6H_4 \rangle$—$CH_2CH_2$— or, respectively, —$CH_2$—$CH_2$—$C_6H_4$—$CH_2$—.

$R^5$ can preferably be H, methyl, ethyl, n-propyl, isopropyl, butyl or phenyl.

Compounds of the general formula I can preferably be: (EtO)$_3$Si—$CH_2$—NH—CO—N=N—CO—NH—$CH_2$—Si(OEt)$_3$, (EtO)$_3$Si—$CH_2$—$CH_2$—NH—CO—N=N—CO—NH—$CH_2$—$CH_2$—Si(OEt)$_3$, (EtO)$_3$Si—$CH_2$—$CH_2$—$CH_2$—NH—CO—N=N—CO—NH—$CH_2$—$CH_2$—$CH_2$—Si(OEt)$_3$, (EtO)$_3$Si—$CH_2$—$CH_2$—$CH_2$—NH—CO—N=N—CO—NH—$CH_2$—$CH_2$—$CH_2$—Si(OEt)$_2$, (EtO)$_3$Si—(CH$_2$)$_{11}$—NH—CO—N=N—CO—NH—(CH$_2$)$_{11}$—Si(OEt)$_3$, (EtO)$_3$Si—(CH$_2$)$_{12}$—NH—CO—N=N—CO—NH—(CH$_2$)$_{12}$—Si(OEt)$_3$, (EtO)$_3$Si—$CH_2CH(CH_3)CH_2$—NH—CO—N=N—CO—NH—$CH_2CH(CH_3)CH_2$—Si(OEt)$_2$, (EtO)$_3$Si—$CH_2$—$CH_2$—$C_6H_4$—$CH_2$—NH—CO—N=N—CO—NH—$CH_2$—$C_6H_4$—$CH_2$—$CH_2$—Si(OEt)$_3$, (EtO)$_3$Si—$CH_2$—$CH_2$—$C_6H_4$—NH—CO—N=N—CO—NH—$C_6H_4$—$CH_2$—$CH_2$—Si(OEt)$_3$, (MeO)$_3$Si—$CH_2$—NH—CO—N=N—CO—NH—$CH_2$—Si(OMe)$_3$, (MeO)$_3$Si—$CH_2$—$CH_2$—NH—CO—N=N—CO—NH—$CH_2$—$CH_2$—Si(OMe)$_3$, (MeO)$_3$Si—$CH_2$—$CH_2$—$CH_2$—NH—CO—N=N—CO—NH—$CH_2$—$CH_2$—$CH_2$—Si(OMe)$_3$, (MeO)$_3$Si—$CH_2$—$CH_2$—$CH_2$—$CH_2$—NH—CO—N=N—CO—NH—$CH_2$—$CH_2$—$CH_2$—$CH_2$—Si(OMe)$_3$, (MeO)$_3$Si—

(CH$_2$)$_{11}$—NH—CO—N=N—CO—NH—(CH$_2$)$_{11}$—Si(OMe)$_3$, (MeO)$_3$Si—(CH$_2$)$_{12}$—NH—CO—N=N—CO—NH—(CH$_2$)$_{12}$—Si(OMe)$_3$, (MeO)$_3$Si—CH$_2$CH(CH$_3$)CH$_2$—NH—CO—N=N—CO—NH—CH$_2$CH(CH$_3$)CH$_2$—Si(OMe)$_3$, (MeO)$_3$Si—CH$_2$—CH$_2$—C$_6$H$_4$—CH$_2$—NH—CO—N=N—CO—NH—CH$_2$—C$_6$H$_4$—CH$_2$—CH$_2$—Si(OMe)$_3$ or (MeO)$_3$Si—CH$_2$—CH$_2$—C$_6$H$_4$—NH—CO—N=N—CO—NH—C$_6$H$_4$—CH$_2$—CH$_2$—Si(OMe)$_3$, where Me=methyl and Et=ethyl.

Compounds of the general formula II can preferably be: H$_2$N—C(O)—N=N—C(O)—NH$_2$, R$^3$—HN—C(O)—N=N—C(O)—NH—R$^4$, particularly preferably Me-HN—C(O)—N=N—C(O)—NH-Me, Et-HN—C(O)—N=N—C(O)—NH-Et, n-Pr—HN—C(O)—N=N—C(O)—NH-n-Pr, iso-Pr—HN—C(O)—N=N—C(O)—NH-iso-Pr, n-Bu-HN—C(O)—N=N—C(O)—NH-n-Bu, sec-Bu-HN—C(O)—N=N—C(O)—NH-sec-Bu, tert-Bu-HN—C(O)—N=N—C(O)—NH-tert-Bu, benzyl-HN—C(O)—N=N—C(O)—NH-benzyl or phenyl-HN—C(O)—N=N—C(O)—NH-phenyl, R$^3$—O—C(O)—N=N—C(O)—O—R$^4$, particularly preferably Et-O—C(O)—N=N—C(O)—O-Et, n-Pr—O—C(O)—N=N—C(O)—O-n-Pr, iso-Pr—O—C(O)—N=N—C(O)—O-iso-Pr, n-Bu-O—C(O)—N=N—C(O)—O-n-Bu, tert-Bu-O—C(O)—N=N—C(O)—O-tert-Bu, sec-Bu-O—C(O)—N=N—C(O)—O-sec-Bu, cyclohexyl-O—C(O)—N=N—C(O)—O-cyclohexyl or benzyl-O—C(O)—N=N—C(O)—O-benzyl, or R$^5$—(O—CH$_2$—CH$_2$)$_n$—O—C(O)—N=N—C(O)—O—(CH$_2$—CH$_2$—O)$_n$—R$^5$ where n=1-10, particularly preferably Me-(O—CH$_2$—CH$_2$)$_n$—O—C(O)—N=N—C(O)—O—(CH$_2$—CH$_2$—O)$_n$-Me, Et-(O—CH$_2$—CH$_2$)$_n$—O—C(O)—N=N—C(O)—O—(CH$_2$—CH$_2$—O)$_n$-Et, n-Pr—(O—CH$_2$—CH$_2$)$_n$—O—C(O)—N=N—C(O)—O—(CH$_2$—CH$_2$—O)$_n$-n-Pr, iso-Pr—(O—CH$_2$—CH$_2$)$_n$—O—C(O)—N=N—C(O)—O—(CH$_2$—CH$_2$—O)$_n$-iso-Pr, n-Bu-(O—CH$_2$—CH$_2$)$_n$—O—C(O)—N=N—C(O)—O—(CH$_2$—CH$_2$—O)$_n$-n-Bu, tert-Bu-(O—CH$_2$—CH$_2$)$_n$—O—C(O)—N=N—C(O)—O—(CH$_2$—CH$_2$—O)$_n$-t-Bu, sec-Bu-(O—CH$_2$—CH$_2$)$_n$—O—C(O)—N=N—C(O)—O—(CH$_2$—CH$_2$—O)$_n$-sec-Bu, cyclohexyl-(O—CH$_2$—CH$_2$)$_n$—O—C(O)—N=N—C(O)—O—(CH$_2$—CH$_2$—O)$_n$-cyclohexyl or benzyl-(O—CH$_2$—CH$_2$)$_n$—O—C(O)—N=N—C(O)—O—(CH$_2$—CH$_2$—O)$_n$-benzyl, where Me=methyl, Et=ethyl, n-Pr=n-propyl, i-Pr=isopropyl, n-Bu=n-butyl, sec-Bu=sec-butyl and tert-Bu=tert-butyl.

Compounds of the general formula III can preferably be: 3-aminopropyl(trimethoxysilane), 3-aminopropyl(triethoxysilane), 3-aminopropyl(diethoxymethoxysilane), 3-aminopropyl(tripropoxysilane), 3-aminopropyl(dipropoxymethoxysilane), 3-aminopropyl(tridodecanoxysilane), 3-aminopropyl(tritetradecanoxysilane), 3-aminopropyl(trihexadecanoxysilane), 3-aminopropyl(trioctadecanoxysilane), 3-aminopropyl(didodecanoxy)tetradecanoxysilane, 3-aminopropyl(dodecanoxy)tetradecanoxy(hexadecanoxy)-silane, 3-aminopropyl(dimethoxymethylsilane), 3-aminopropyl(methoxydimethylsilane), 3-aminopropyl(hydroxydimethylsilane), 3-aminopropyl(diethoxymethylsilane), 3-aminopropyl(ethoxydimethylsilane), 3-aminopropyl(dipropoxymethylsilane), 3-aminopropyl(propoxydimethylsilane), 3-aminopropyl(diisopropoxymethylsilane), 3-aminopropyl(isopropoxydimethylsilane), 3-aminopropyl(dibutoxymethylsilane), 3-aminopropyl(butoxydimethylsilane), 3-aminopropyl(disiobutoxymethylsilane), 3-aminopropyl(isobutoxydimethylsilane), 3-aminopropyl(didodecanoxymethylsilane), 3-aminopropyl(dodecanoxydimethylsilane), 3-aminopropyl(ditetradecanoxymethylsilane), 3-aminopropyl(tetradecanoxydimethylsilane), 2-aminoethyl(trimethoxysilane), 2-aminoethyl(triethoxysilane), 2-aminoethyl(diethoxymethoxysilane), 2-aminoethyl(tripropoxysilane), 2-aminoethyl(dipropoxymethoxysilane), 2-aminoethyl(tridodecanoxysilane), 2-aminoethyl(tritetradecanoxysilane), 2-aminoethyl(trihexadecanoxysilane), 2-aminoethyl(trioctadecanoxysilane), 2-aminoethyl(didodecanoxy)tetradecanoxysilane, 2-aminoethyl(dodecanoxy)tetradecanoxy(hexadecanoxy) silane, 2-aminoethyl(dimethoxymethylsilane), 2-aminoethyl(methoxydimethylsilane), 2-aminoethyl(diethoxymethylsilane), 2-aminoethyl(ethoxydimethylsilane), 1-aminomethyl(trimethoxysilane), 1-aminomethyl(triethoxysilane), 1-aminomethyl(diethoxymethoxysilane), 1-aminomethyl(dipropoxymethoxysilane), 1-aminomethyl(tripropoxysilane), 1-aminomethyl(trimethoxysilane), 1-aminomethyl(dimethoxymethylsilane), 1-aminomethyl(methoxydimethylsilane), 1-aminomethyl(diethoxymethylsilane), 1-aminomethyl(ethoxydimethylsilane), 3-aminobutyl(trimethoxysilane), 3-aminobutyl(triethoxysilane), 3-aminobutyl(diethoxymethoxysilane), 3-aminobutyl(tripropoxysilane), 3-aminobutyl(dipropoxymethoxysilane), 3-aminobutyl(dimethoxymethylsilane), 3-aminobutyl(diethoxymethylsilane), 3-aminobutyl(dimethylmethoxysilane), 3-aminobutyl(dimethylethoxysilane), 3-aminobutyl(tridodecanoxysilane), 3-aminobutyl(tritetradecanoxysilane), 3-aminobutyl(trihexadecanoxysilane), 3-aminobutyl(didodecanoxy)tetradecanoxysilane, 3-aminobutyl(dodecanoxy)tetradecanoxy(hexadecanoxy) silane, 3-amino-2-methylpropyl(trimethoxysilane), 3-amino-2-methylpropyl(triethoxysilane), 3-amino-2-methylpropyl(diethoxymethoxysilane), 3-amino-2-methylpropyl(tripropoxysilane), 3-amino-2-methylpropyl(dipropoxymethoxysilane), 3-amino-2-methylpropyl(tridodecanoxysilane), 3-amino-2-methylpropyl(tritetradecanoxysilane), 3-amino-2-methylpropyl(trihexadecanoxysilane), 3-amino-2-methylpropyl(trioctadecanoxysilane), 3-amino-2-methylpropyl(didodecanoxy)tetradecanoxy-silane, 3-amino-2-methylpropyl(dodecanoxy)tetradecanoxy-(hexadecanoxy)silane, 3-amino-2-methylpropyl(dimethoxymethylsilane), 3-amino-2-methylpropyl(methoxydimethylsilane), 3-mercapto-2-methylpropyl(diethoxymethylsilane), 3-mercapto-2-methylpropyl(ethoxydimethylsilane), 3-mercapto-2-methylpropyl(dipropoxymethylsilane), 3-amino-2-methylpropyl(propoxydimethylsilane), 3-amino-2-methylpropyl(diisopropoxymethylsilane), 3-amino-2-methylpropyl(isopropoxydimethylsilane), 3-amino-2-methylpropyl(dibutoxymethylsilane), 3-amino-2-methylpropyl(butoxydimethylsilane), 3-amino-2-methylpropyl(disiobutoxymethylsilane), 3-amino-2-methylpropyl(isobutoxydimethylsilane), 3-amino-2-methylpropyl(didodecanoxymethylsilane), 3-amino-2-methylpropyl(dodecanoxydimethylsilane), 3-amino-2-methylpropyl(ditetradecanoxymethylsilane) or 3-amino-2-methylpropyl(tetradecanoxydimethylsilane).

The product obtainable via the process according to the invention can comprise silicon-containing azobis-carbamides of the general formula I in a purity greater than 30 mol %, preferably greater than 50 mol %, particularly preferably greater than 75 mol %, very particularly preferably greater than 85 mol %.

The relative percentage contents of the compounds of the general formula I in the product obtained via the process according to the invention are determined via integration of the $^{13}$C NMR integrals of the target product of the general formula I and comparison with the totality of the $^{13}$C NMR integrals.

The reaction can be carried out in solvents or with no solvent.

The amount of solvent, as a ratio to the amounts used of the compounds of the general formula II, can be from 1% by weight to 5000% by weight, preferably from 1% by weight to 1000% by weight, particularly preferably from 50% by weight to 1000% by weight, particularly preferably from 50% by weight to 500% by weight.

The amount of solvent, as a ratio to the amounts used of the compounds of the general formula II, can be more than 1% by weight, preferably more than 10% by weight, particularly preferably more than 50% by weight and very particularly preferably more than 100% by weight.

The boiling point of the solvent can be from −100° C. to 250° C., preferably from 0 to 150° C., particularly preferably from 20 to 100° C.

Solvents used can comprise an alcoholic or non-alcoholic compound.

Solvents used can comprise mixtures of alcoholic and non-alcoholic compounds.

Non-alcoholic solvents can be halogen-containing or halogen-free solvents.

Halogen-containing solvents can preferably be $CCl_4$, $CHCl_3$, $CH_2Cl_2$, $CH_3Cl$, $CCl_3$—$CCl_3$, $CHCl_2$—$CCl_3$, $CHCl_2$—$CHCl_2$ or $CH_2Cl$—$CH_2Cl$.

Non-alcoholic, halogen-free solvents used can comprise alkanes, alkyl carbonates, aromatics, substituted aromatics, preferably alkyl-substituted aromatics, particularly preferably toluene, p-xylene, m-xylene or o-xylene, ethers, mercaptans, dialkyl sulphides, trialkylamines, alkylphosphanes or arylphosphanes.

Alkanes used can preferably comprise pure alkanes or a mixture of alkanes, examples being pentane, hexane, cyclohexane, heptane or octane.

Alkyl carbonates used can comprise open-chain or cyclic carbonates.

Open-chain alkyl carbonates used can preferably comprise dimethyl carbonate, diisopropyl carbonate or diethyl carbonate.

Cyclic alkyl carbonates used can preferably comprise ethylene carbonate, 1-methylethylene carbonate, propylene carbonate or glycerol carbonate.

Alcoholic solvents used can comprise straight-chain, branched or else cyclic alcohols.

Alcohols used can also comprise mixtures of alcohols.

It is particularly preferably possible to use alcohols which correspond to the respective alkoxy substituents on the silicon in the compounds of the formulae I and III, and also isopropanol and tert-butanol.

Alcoholic solvent used can very particularly preferably comprise methanol, ethanol and isopropanol.

The reaction can preferably be carried out with exclusion of air and/or with exclusion of water.

The reaction can be carried out under an inert gas atmosphere, for example under argon or nitrogen, preferably under nitrogen.

The process according to the invention can be carried out at atmospheric pressure, at elevated pressure or at reduced pressure.

Preference is given to atmospheric pressure and to reduced pressure.

Elevated pressure can be a pressure of from 1.1 bar to 100 bar, preferably from 1.5 bar to 50 bar, particularly preferably from 2 bar to 20 bar and very particularly preferably from 2 bar to 10 bar.

Reduced pressure can be a pressure from 1 mbar to 1000 mbar, preferably from 1 mbar to 500 mbar, particularly preferably from 1 mbar to 250 mbar, very particularly preferably from 5 mbar to 100 mbar.

The process according to the invention can be carried out at from −50° C. to +200° C., preferably from −25° C. to 150° C., particularly preferably from −10° C. to 100° C., very particularly preferably from −10° C. to 50° C.

In the process according to the invention, compounds of the general formula II can be added to compounds of the general formula III.

In the process according to the invention, compounds of the general formula III can be added to compounds of the general formula II.

In the process according to the invention, the azobiscarboxy compounds of the general formula II can be added to aminosilanes of the general formula III in a molar ratio of from 1:1.80 to 1:2.25, preferably from 1:1.90 to 1:2.15, and particularly preferably in a ratio of from 1:1.95 to 1:2.05.

In the reaction of azobiscarboxy compounds of the general formula II with aminosilanes of the general formula III, stabilizers can be added prior to, during or after the reaction.

Stabilizers can be monomers, oligomers or polymers.

Preference is given to oligomers and polymers.

Stabilizers can inhibit or delay the thermal decomposition of azo compounds.

Stabilizers can be free-radical scavengers.

Stabilizers can inhibit or delay the light-induced decomposition of azo compounds.

Stabilizers can be UV stabilizers.

Stabilizers can inhibit or delay oxidation reactions.

Stabilizers can be anionic or cationic compounds.

Stabilizers can comprise heteroatoms, such as oxygen, sulphur, nitrogen or phosphorus.

The amount of stabilizers that can be used in the process according to the invention is from 0.001 to 100% by weight, preferably from 0.01 to 50% by weight, particularly preferably from 0.01 to 10% by weight, very particularly preferably from 0.1 to 5% by weight, based on the mass of the material used of the general formula II.

The amount of stabilizers used in the process according to the invention can be more than 0.001% by weight, preferably more than 0.01% by weight, particularly preferably more than 0.1% by weight, very particularly preferably more than 1% by weight, based on the mass of the material used of the general formula II.

The amount of stabilizers used in the process according to the invention can be less than 100% by weight, preferably less than 25% by weight, particularly preferably less than 10% by weight, but very particularly preferably more than 1% by weight, based on the mass of the material used of the general formula II.

The residual content of compounds of the general formula II in the product produced by the process according to the invention can be less than 25 mol %, preferably less than 10 mol %, particularly preferably less than 5 mol %, very particularly preferably less than 3 mol %.

The relative mol % values for the compounds of the general formula II in the product produced by the process according to the invention are determined via integration of the carbonyl C atoms in the $^{13}$C NMR, with respect to the mol % values for the compounds of the general formula I.

The residual content of compounds of the general formula III in the product produced by the process according to the invention can be less than 25 mol %, preferably less than 10 mol %, particularly preferably less than 5 mol %, very particularly preferably less than 3 mol %.

Relative mol % values for compounds of the formula III= (integral of all of the C atoms of $R^I$ of the formula III adjacent to N)/((integral of all of the C atoms of $R^I$ of the formula III adjacent to N)+(integral of all of the C atoms of $R^I$ of the formula I adjacent to N)).

For the substance $NH_2$—$CH_2$—$CH_2$—$CH_2$—$Si(OEt)_3$ of the formula III, by way of example, the integral of the following C atoms $NH_2$—$\underline{CH_2}$- is used to determine the relative contents.

For the substance $[(EtO)_3Si$—$CH_2$—$CH_2$—$CH_2$—$NH$—$C(\!=\!O)$—$N\!=\!]_2$ of the formula I, by way of example, the integral of the following C atoms —$\underline{CH_2}$—$NH$—$C(\!=\!O)$—$N\!=$ is used to determine the relative contents.

The product produced by the process according to the invention can comprise compounds of the general formula IV, V and/or VI

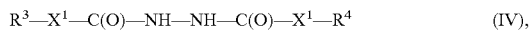

$$R^3—X^1—C(O)—NH—NH—C(O)—X^1—R^4 \qquad (IV),$$

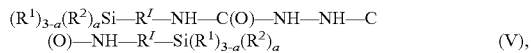

$$(R^1)_{3-a}(R^2)_aSi—R^I—NH—C(O)—NH—NH—C(O)—NH—R^I—Si(R^1)_{3-a}(R^2)_a \qquad (V),$$

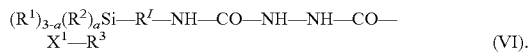

$$(R^1)_{3-a}(R^2)_aSi—R^I—NH—CO—NH—NH—CO—X^1—R^3 \qquad (VI).$$

The silicon-containing azodicarbamides of the general formula I can be used as coupling agents between inorganic materials, e.g. glass beads, glass fragments, glass surfaces, glass fibres, or oxidic fillers, preferably silicas, e.g. precipitated silicas and fumed silicas, and organic polymers, e.g. thermosets, thermoplastics or elastomers, or, respectively, as crosslinking agents and surface-modifiers for oxidic surfaces.

The silicon-containing azodicarbamides of the general formula I can be used as coupling reagents in filled rubber mixtures, e.g. tyre treads, technical rubber items or shoe soles.

An advantage of the process according to the invention is that it is possible to produce silicon-containing azodicarbamides of the general formula I in a single synthetic step from synthetic units familiar in industry.

Another advantage of the process according to the invention is that there is no requirement for the oxidation of hydrazine derivatives, and high yields are achieved, as also are high purities.

Another advantage of the process according to the invention is that there is no requirement for any complicated purification of the products obtained.

EXAMPLES

The following raw materials are used for the examples:
Diisopropyl azodicarboxylate (Jayhawk Chemicals) with >94% purity (GC/thermal conductivity detector).
3-Aminopropyl(triethoxysilane) from Evonik Degussa GmbH with >98% purity (GC/thermal conductivity detector).
Pentane, $CH_2Cl_2$ and isopropanol from Aldrich, Acros and Merck-Schuchardt.

Example 1

Production of $[(EtO)_3Si$—$(CH_2)_3$—$NH$—$C(\!=\!O)$—$N\!=\!]_2$ in Pentane 164.2 g (742 mmol) of 3-aminopropyl(triethoxysilane) were used as initial charge in 1000 g of pentane at 0° C. in a flask under inert gas, and stirred. 75 g of diisopropyl azodicarboxylate (DIAD, 371 mmol) were added dropwise at from −5° C. to 5° C. to the solution within a period of 30 min. Stirring was then continued for a further 30 min at from −5° C. to 5° C. The cooling bath is then removed and the solution is stirred for 180 min, while the temperature of the mixture increased to room temperature. All of the volatile constituents (pentane, isopropanol) are then removed on a rotary evaporator at a pressure of up to 6 mbar.

NMR studies show that the red oil obtained (194 g, >99% yield) comprises the target product in >85 mol % purity.

Example 2

Production of $[(EtO)_3Si$—$(CH_2)_3$—$NH$—$C(\!=\!O)$—$N\!=\!]_2$ in $CH_2Cl_2$ 164 g (742 mmol) of 3-aminopropyl(triethoxysilane) were used as initial charge in 1000 g of $CH_2Cl_2$ at 0° C. in a flask under inert gas, and stirred. 75 g of diisopropyl azodicarboxylate (DIAD, 371 mmol) were added dropwise at from −5° C. to 5° C. to the solution within a period of 30 min. Stirring was then continued for a further 30 min at from −5° C. to 5° C. The cooling bath is then removed and the solution is stirred for 170 min, while the temperature of the mixture increased to room temperature. All of the volatile constituents ($CH_2Cl_2$, isopropanol) are then removed on a rotary evaporator at a pressure of up to 6 mbar.

NMR studies show that the red oil obtained (193.8 g, >99% yield) comprises the target product in >85 mol % purity.

The invention claimed is:

1. Process for producing silicon-containing azo-dicarbamides of the general formula I

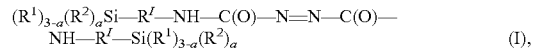

$$(R^1)_{3-a}(R^2)_aSi—R^I—NH—C(O)—N\!=\!N—C(O)—NH—R^I—Si(R^1)_{3-a}(R^2)_a \qquad (I),$$

via reaction of azobiscarboxy compounds of the general formula II

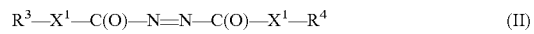

$$R^3—X^1—C(O)—N\!=\!N—C(O)—X^1—R^4 \qquad (II)$$

with aminosilanes of the general formula III

$$(R^1)_{3-a}(R^2)_aSi—R^I—NH_2 \qquad (III),$$

where a is mutually independently 1, 2 or 3,
$R^1$ are mutually independently substituted or unsubstituted C1-C18-alkyl groups, C5-C18-cycloalkyl groups, or C6-C18-aryl groups,
$R^2$ are mutually independently an —OH, a substituted or unsubstituted C1-C18-alkoxy group or a C5-C18-cycloalkoxy group, R' is a branched or unbranched, saturated or unsaturated, aliphatic, aromatic or mixed aliphatic/aromatic divalent $C_1$-$C_{30}$-hydrocarbon group, optionally substituted with F—, Cl—, Br—, I—, —CN or HS—, $X^1$ are mutually independently O, NH or N-$A^1$, where $A^1$ is C1-C12-alkyl group or aryl group and $R^3$ and $R^4$ are mutually independently an H, a C1-C18-alkyl group, a benzyl group (—$CH_2$—$C_6H_5$) or an alkyl polyether group of the formula ($CH_2$—$CH_2$—O)$_n$—$R^5$ or ($CH(CH_3)$—$CH_2$—O)$_n$—$R^5$, where the average of n is from 1 to 18 and $R^5$ is mutually independently a branched or unbranched, saturated or unsaturated monovalent C1-C32-hydrocarbon chain.

2. Process for producing silicon-containing azocarbamides according to claim 1, wherein the azobiscarboxy compound of the general formula II is $H_2N$—C(O)—N=N—C(O)—$NH_2$, $R^3$—O—C(O)—N=N—C(O)—O—$R^4$ or $R^3$—HN—C(O)—N=N—C(O)—NH—$R^4$.

3. Process for producing silicon-containing azocarbamides according to claim 1 or 2, wherein the aminosilane of the general formula III is 3-aminopropyl(trimethoxy-silane), 3-aminopropyl(triethoxysilane), 3-aminopropyl(dimethoxymethylsilane), 3-aminopropyl(methoxydimethylsilane), 3-aminopropyl(diethoxymethylsilane), 3-aminopropyl(ethoxydimethylsilane) or 3-aminopropyl(tripropoxysilane).

4. Process for producing silicon-containing azo-dicarbamides according to claim 1, wherein the reaction is carried out in a solvent.

5. Process for producing silicon-containing azo-dicarbamides according to claim 1, wherein the reaction is carried out with no solvent.

6. Process for producing silicon-containing azo-dicarbamides according to claim 1, wherein the reaction is carried out with exclusion of air and/or with exclusion of water.

7. Process for producing silicon-containing azocarbamides according to claim 1, wherein prior to, during or after the reaction stabilizers are added.

8. Process for producing silicon-containing azo-dicarbamides according to claim 2, wherein the compound used of the general formula II is $C_3H_7$—O—C(O)—N=N—C(O)—O—$C_3H_7$ or $C_6H_4$—$CH_2$—O—C(O)—N=N—C(O)—O—$CH_2$—$C_6H_4$.

9. Process for producing silicon-containing azo-dicarbamides according to claim 1, wherein the reaction is carried out at temperatures from −50° C. to +200° C.

* * * * *